(12) United States Patent
Matlock et al.

(10) Patent No.: US 8,801,695 B2
(45) Date of Patent: Aug. 12, 2014

(54) TRACHEOSTOMY TUBE CONNECTOR KEY SYSTEM

(75) Inventors: George L. Matlock, Pleasanton, CA (US); Steven M. Brackney, Livermore, CA (US); Avila Ignacio, Modesto, CA (US)

(73) Assignee: Covidien LP, Cupertino, CA (US)

( * ) Notice: Subject to any disclaimer, the term of this patent is extended or adjusted under 35 U.S.C. 154(b) by 276 days.

(21) Appl. No.: 11/823,438

(22) Filed: Jun. 27, 2007

(65) Prior Publication Data

US 2007/0255258 A1 Nov. 1, 2007

Related U.S. Application Data

(63) Continuation-in-part of application No. 11/237,168, filed on Sep. 28, 2005, now Pat. No. 7,647,929.

(51) Int. Cl.
*A61M 25/16* (2006.01)
*A61M 25/18* (2006.01)
*A61M 5/178* (2006.01)
*A61M 25/00* (2006.01)

(52) U.S. Cl.
USPC . 604/535; 604/158; 604/164.01; 604/164.07; 604/165.01; 604/165.02; 604/165.04; 604/264; 604/523; 604/533; 604/534

(58) Field of Classification Search
USPC ............... 604/158, 164.01, 164.07, 165.01, 604/165.02, 165.03, 165.04, 166.01, 93.01, 604/27, 43, 264, 275, 523, 533, 534, 535; 128/200.26, 207.14, 911, 912, DIG. 26
See application file for complete search history.

(56) References Cited

U.S. PATENT DOCUMENTS

| | | | | |
|---|---|---|---|---|
| 3,039,469 | A | * | 6/1962 | Fountain .................. 128/200.26 |
| 3,225,767 | A | * | 12/1965 | Smith ...................... 128/200.26 |
| 4,304,228 | A | * | 12/1981 | Depel ...................... 128/200.26 |
| 4,315,505 | A | * | 2/1982 | Crandall et al. ......... 128/200.26 |
| 4,909,248 | A |   | 3/1990 | McLennan Anderson |

(Continued)

FOREIGN PATENT DOCUMENTS

| WO | WO9107201 | 5/1991 |
|---|---|---|
| WO | WO9213587 | 8/1992 |

(Continued)

OTHER PUBLICATIONS

International Search Report PCT/US2008/0068610, 5 pages, mailed Oct. 1, 2008.

(Continued)

*Primary Examiner* — Kevin C Sirmons
*Assistant Examiner* — Shefali Patel
(74) *Attorney, Agent, or Firm* — Fletcher Yoder PC

(57) ABSTRACT

A tracheostomy tube is provided. The tracheostomy tube includes an outer cannula that comprises an outer cannula connector comprising a first keying feature. The tracheostomy tube further comprises an inner cannula comprising an inner cannula connector including a second keying feature configured to complement the first keying feature when the inner cannula is inserted into the outer cannula. Further, a method is provided, whereby the method comprises inserting an outer cannula into a patient's trachea, and inserting an inner cannula into the outer cannula such that a keying feature on an inner cannula connector of the inner cannula engages a second keying feature on an outer cannula connector of the outer cannula.

14 Claims, 9 Drawing Sheets

(56) References Cited

U.S. PATENT DOCUMENTS

| | | |
|---|---|---|
| 4,976,261 A | 12/1990 | Gluck et al. |
| 5,038,766 A | 8/1991 | Parker |
| 5,067,496 A * | 11/1991 | Eisele .................. 128/207.15 |
| 5,174,283 A | 12/1992 | Parker |
| 5,285,778 A | 2/1994 | Mackin |
| 5,303,697 A | 4/1994 | Brain |
| 5,390,669 A | 2/1995 | Stuart et al. |
| 5,419,314 A * | 5/1995 | Christopher ............ 128/200.26 |
| 7,503,328 B2 | 3/2009 | Kolobow et al. |
| 2003/0196659 A1 | 10/2003 | Gradon et al. |
| 2006/0019218 A1 * | 1/2006 | Kuo ............................... 433/166 |
| 2007/0068531 A1 | 3/2007 | Matlock et al. |

FOREIGN PATENT DOCUMENTS

| | | |
|---|---|---|
| WO | WO 9323103 A1 * | 11/1993 |
| WO | WO9533506 A | 12/1995 |
| WO | WO 2007/038562 A | 4/2007 |

OTHER PUBLICATIONS

Teleflex Medical: Rusch; Disposable Inner Cannula, 2009, 5 pgs.

\* cited by examiner

TRACHEOSTOMY TUBE CONNECTOR KEY SYSTEM

CROSS REFERENCE TO RELATED APPLICATIONS

This application is a Continuation-in-Part of U.S. patent application Ser. No. 11/237,168, now U.S. Pat. No. 7,647,929, titled "Medical Device Tube Having a Flange With Opposing Support Ears for Improved Alignment and Retention of an Inner Cannula in an Outer Cannula," filed Sep. 28, 2005, herein incorporated by reference in its entirety.

BACKGROUND OF THE INVENTION

1. Field of the Invention

The present disclosure, according to one embodiment, relates to medical device tubes, e.g., tracheostomy tubes, used in medical applications, and more particularly, to more securely attaching an inner cannula to an outer cannula of a trachostomy tube.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

A medical device tube may include an outer cannula (slender tube that may be inserted into a body cavity) attached to a head base connector. The head base connector and outer cannula are adapted for insertion of a disposable inner cannula. One example of a medical device tube is a tracheostomy tube. The tracheostomy tube may have a curved "L" shape and the head base connector may be attached to a swivel neck plate/flange. The tracheostomy tube provides an artificial airway for access to the patient's airway for airway management. The tracheostomy tube is introduced into a tracheotomy incision in the patient's neck that provides access to the trachea. The tracheostomy tube may be secured by a swivel neck plate/flange that may be connected to a tracheostomy tube holder or neck strap, thus securing this artificial airway for spontaneous or mechanical ventilation of the patient.

The inner cannula may be inserted into the head base connector and outer cannula after the tracheostomy tube has been placed into the patient's trachea. This inner cannula typically includes a connector for quick removal of the inner cannula from the outer cannula, e.g., the inner cannula connector removably attaches to the head base connector, so that the inner cannula may be removed quickly if an obstruction, e.g., plug of mucus, sputum, etc., is formed. For example, a snap connector may be used to attach the inner cannula to the outer cannula. A mechanical ventilator hose may be removably coupled to the inner cannula to assist the patient in breathing. However, if the inner cannula is twisted and/or put into radial torsion during use, e.g., caused by movement of the ventilator hose connected thereto, the snap connector may disengage and allow the inner cannula to withdraw from the outer cannula.

Further, varying sizes of inner cannulas and/or outer cannulas, exist so as to accommodate patients having tracheas of different sizes. Thus, a clinician may be provided with a variety of sizes of inner and/or outer cannulas that may lead to confusion as to the proper size of inner cannula to insert in an outer cannula. This confusion may be exacerbated if the inner cannula is close to the right size and if the improperly matched inner and outer cannula can still be engaged with one another. However, the apparent fitting of the outer and inner cannulas may conceal their mismatch, such that the patient may be improperly fitted with the tracheostomy tube.

SUMMARY

Improving the reliability of attachment and continued attachment retention of the inner cannula to the outer cannula may be desired. Also, an added benefit would be to do so without having to change existing designs for the inner cannula and connector.

In accordance with embodiments of the present technique, a medical device tube is provided. The medical device tube includes an outer cannula comprising an outer cannula connector. The outer cannula connector comprises a first keying feature. The medical device tube further includes an inner cannula having an inner cannula connector. The inner cannula connector includes a second keying feature configured to complement the first keying feature when the inner cannula is inserted into the outer cannula.

In accordance with embodiments of the present technique an inner cannula assembly is provided. The inner cannula comprises an inner cannula, and an inner cannula connector comprising a keying feature. The keying feature is configured to prevent insertion of the inner cannula into a differently sized outer cannula.

In accordance with embodiments of the present technique, an outer cannula assembly is provided. The outer cannula assembly comprises an outer cannula, and an outer cannula connector comprising two or more support ears. Further, the two or more support ears are configured to substantially prevent rotation of an inner cannula connector when the inner cannula connector is engaged with the outer cannula connector.

In accordance with embodiments of the present technique, a medical device tube is provided. The medical device tube comprises an outer cannula comprising an outer cannula connector. Further, the outer cannula connector comprises two or more support ears; and an inner cannula comprising an inner cannula connector comprising one or more locking ears. Accordingly, the one or more locking ears engage the two or more support ears to substantially prevent rotation of the inner cannula connector relative to the outer cannula connector when the inner cannula connector is engaged with the outer cannula connector.

In accordance with embodiments of the present technique a method is provided including inserting an outer cannula into a patient's trachea. The method further includes inserting an inner cannula into the outer cannula such that a keying feature on an inner cannula connector of the inner cannula engages a complementary keying feature on an outer cannula connector of the outer cannula.

BRIEF DESCRIPTION OF THE DRAWINGS

Advantages of the invention may become apparent upon reading the following detailed description and upon reference to the drawings in which.

Figure 1:
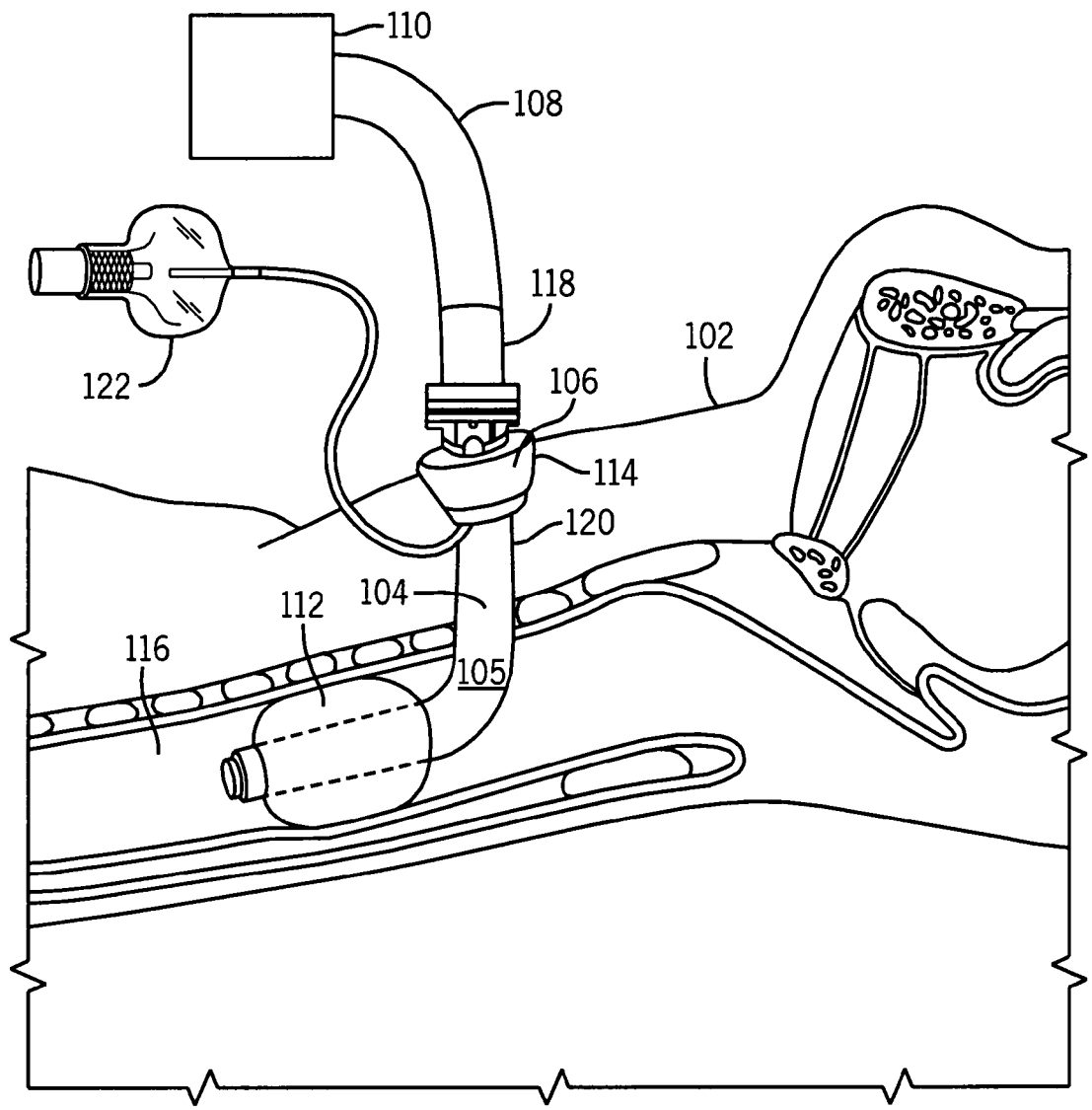
FIG. 1 illustrates a schematic diagram of a patient ventilation system, in accordance with an embodiment of the present technique.

While the present disclosure is susceptible to various modifications and alternative forms, specific example embodiments thereof have been shown in the drawings and are herein described in detail. It should be understood, however, that the description herein of specific example embodiments is not intended to limit the disclosure to the particular forms disclosed herein, but on the contrary, this disclosure is to cover all modifications and equivalents as defined by the appended claims.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Referring now to the drawings, the details of specific example embodiments are schematically illustrated. Like elements in the drawings will be represented by like numbers, and similar elements will be represented by like numbers with a different lower case letter suffix.

Referring to FIG. 1, depicted is a schematic diagram of a patient ventilation system, according to a specific example embodiment of the present disclosure. A patient 102 has a stoma 114 (opening) leading to his/her trachea 116 in which an outer cannula 104 is inserted. The outer cannula 104 may have a curved portion 105, e.g., L shape. A neck flange 106 may be attached to the patient's 102 neck, e.g., by tape and/or straps, etc. (not shown). A ventilator hose 108 may couple a ventilator 110 to a hose coupling 118. Optionally, an inflation collar 112 may be proximate to the outer wall of the outer cannula 104, and an inflation lumen 120 may be within the wall of the outer cannula 104 or proximate thereto. An air valve port 122 may be used in combination with the inflation lumen 120 and the inflation collar 112 for, when inflated, creating an air and/or liquid sealing function between the outer cannula 104 and the trachea 116 air passage. The inflation collar 112 may also position the outer cannula 104 in the trachea 116. More than one lumen may be in the wall of the cannula 104 and the additional lumens therein may be used for various other purposes. The inflation collar 112 may be inflated with a fluid, e.g., air, nitrogen, saline, water, etc.

Figure 2:
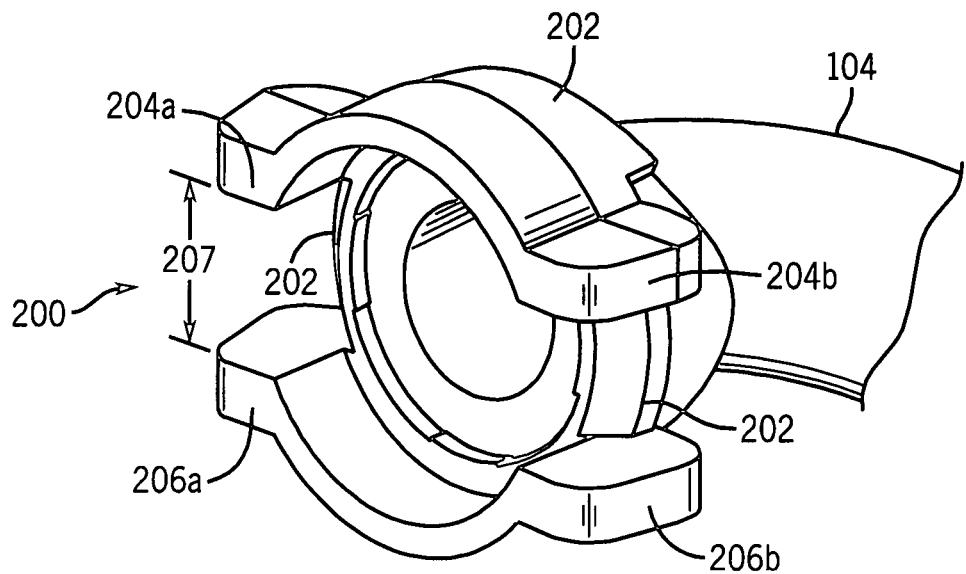
FIG. 2 illustrates a schematic diagram of an outer cannula connector comprising a locking flange having opposing support ears, according to a specific example embodiment of the present disclosure.

Referring to FIG. 2, depicted is a schematic diagram of an outer cannula connector comprising a locking flange having opposing support ears, according to a specific example embodiment of the present disclosure. An outer cannula connector, generally represented by the numeral 200, comprises an outer cannula locking flange 202, a first set of support ears 204a and 204b and a second set of support ears 206a and 206b. The outer cannula connector may be coupled to a proximal end of the outer cannula 104. The second set of support ears 206 are opposite to the first set of support ears 204, e.g., the first and second sets of support ears 204 and 206, respectively, are on opposing sides of each other. Shown are opposing pairs of support ears, however, a single first support ear 204a and a single second support ear 206a opposing the single first support ear 204a may be utilized in accordance with the teachings of this disclosure. It is also contemplated and within the scope of this disclosure that a plurality of opposing support ears may be utilized.

As depicted, in one exemplary embodiment, the support ears 204a, 204b, 206a and 206b extend beyond the outer cannula locking flange 202, forming two diametrically opposed restraining structures adapted to secure complementary or corresponding structures of an inner cannula, as further discussed below. The supporting ears 204a, 204b and/or 206a, 206b form continuous structures that partially encompasses the circumference of the outer cannula connector 200. In the depicted embodiment, the support ears 204a, 204b and/or 206a, 206b extend radially outward, such as between about 2 mm to about 5 mm, from the outermost edge of the locking flange 202 so as to form two the engagement gaps 207. In one implementation the support ears 204 and 206 extend about 3 mm from the outermost edge of the locking flange 202. In one implementation the engagement gaps 207 thus formed are between about 6 to about 10 mm across and in one embodiment the engagement gaps 207 are about 8 mm across. When engaged by the corresponding structures of an inner cannula, the support ears 204 and 206 prevent rotation or swiveling of the inner cannula within the outer cannula 104 and outer cannula connector 200. In other words, the spacing between opposed support ears 204a and 206a and between 204b and 206b is such that the engaging structure of the inner cannula is prevented from rotating by the opposing support ears 204 and 206.

The outer cannula 104 may be formed of, for example, polyvinyl chloride (PVC), polycarbonate, ABS, polystyrene, or other plastic materials, metals, carbon fibers, etc., having suitable biocompatibility with patient tissues. When forming the outer cannula 104, material grade, durometer rating, plasticity, etc., may be chosen for each of the above materials so that the outer cannula 104 has the desired mechanical characteristics, such as rigidity, flexibility, and so forth.

The outer cannula 104 may be formed using injection molding techniques or other conventional molding techniques used to shape and form the outer cannula material, such as PVC. For example, a tube of material (such as PVC in one example) in a moldable state (such as in a molten state) may be inserted into a mold having a specified shape, i.e., length, curvature, tube circumference and so forth, corresponding to the outer cannula 104. While in the mold and while in the moldable state, air may be injected at pressure into the molten tube, forcing the tube into conformity with the mold such that, upon setting and removal from the mold, an outer cannula 104 having the desired characteristics is formed.

Similarly, the outer cannula connector 200 may be formed from PVC, polycarbonate (such as: Lexan® 104-803), ABS, polystyrene, or other plastic materials, metals, carbon fibers, etc., having suitable biocompatibility. When forming the outer cannula connector 200, material grade, durometer rating, plasticity, etc., may be chosen for each of the above materials so that the outer cannula connector 200 has the desired mechanical characteristics, such as rigidity, flexibility, and so forth. In one such implementation, the outer cannula connector 200 is formed from PVC having a higher durometer than the corresponding outer cannula 104, i.e., the outer cannula connector 200 is harder than the outer cannula 104. In one such implementation, the outer cannula connector 200 is formed as a single piece, for example, by molding techniques, such as conventional molding techniques used to shape and form solid PVC parts. For example, a quantity of material (such as PVC in one example) in a moldable state (such as in a molten state) may be injected into a mold having a specified shape, i.e., dimensions, shape, curvature and so forth, corresponding to the outer cannula connector 200. Upon setting and removal from the mold, an outer cannula connector 200 having the desired characteristics is formed.

In such an embodiment, the outer cannula connector 200 and the outer cannula 104 may be attached together by, for example, adhesive bonding, ultrasonic bonding, heat staking, solvent bonding; mechanical snaps, threads and pins, etc. Energy directors, such as those discussed below with reference to FIG. 3, may be used when the material used for the outer cannula connector 200 and outer cannula 104 are ultrasonically welded or heat staked together. Other assembly methods may be used, such as solvent bonding, adhesive bonding, or heat staking, spin welding, mechanical snaps or threads, pins, etc., to fuse the outer cannula locking connector 200 to the outer cannula 104.

Figure 3:
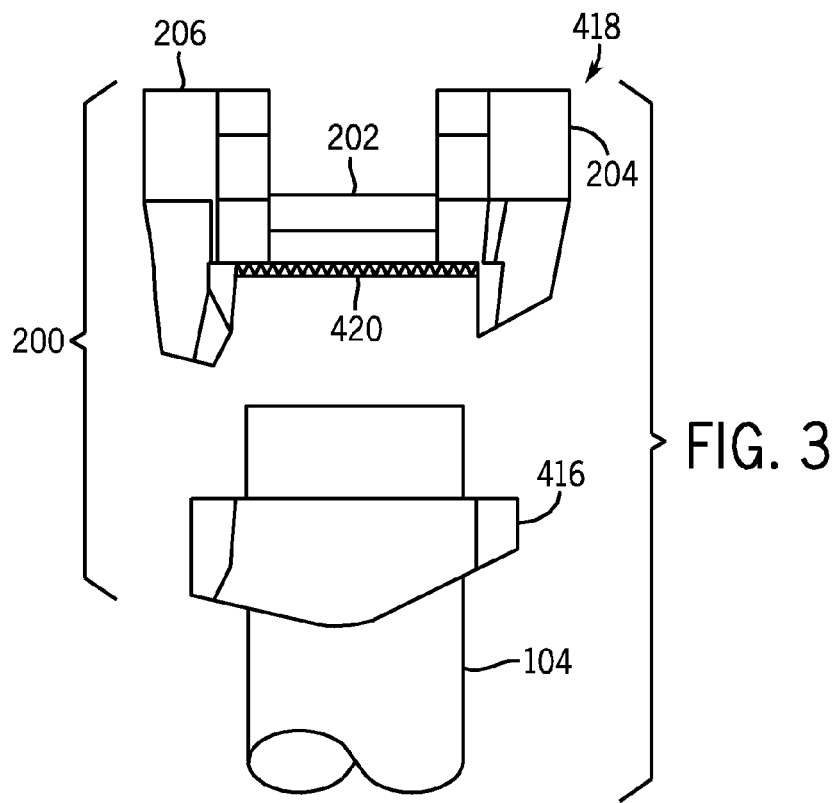
FIG. 3 illustrates an exploded assembly view schematic diagram of the outer cannula connector shown in FIG. 2.

The embodiments discussed above with regard to FIG. 2 generally describe an outer cannula connector 200 employed as a single piece, though one of ordinary skill will appreciate that outer cannula connector 200 may be formed as one piece or as multiple joined pieces. For example, in some embodiments, the outer cannula connector 200 may be formed from separate pieces, some of which may be disposed on the outer cannula 104 prior to being joined to form the outer cannula connector 200. That is, the outer cannula connector 200 can be formed by joining various substructures using bonding methods similar to those described above. Accordingly, referring to FIG. 3, depicted is an exploded assembly view schematic diagram of the outer cannula connector 200 shown in FIG. 2. The outer cannula connector 200 may be comprised of a snap-flange hood 418 and a cannula coupling connector 416. The cannula coupling connector 416 may be attached to a proximal end of the outer cannula 104. The snap-flange hood 418 may be comprised of opposing support ears, e.g., the first and second sets of opposing support ears 204 and 206, respectively, and the flange 202.

In the illustrated embodiment, the support ears 204 and 206 extend sufficiently above and outward from the cannula locking flange 202 so as to prevent the rotation of locking ears 312 (discussed below in FIG. 4) when properly engaged. In particular, sizing of the engagement gap 207 to conform closely to the corresponding width of the locking ears 312 (FIG. 4) generally prevents an inner cannula connector 310 (FIG. 4) from rotating or swiveling relative to the outer cannula adapter 200. Further the support ears 204 and 206 are provided with sufficient height relative to the locking flange 202 that the locking ears 312 (FIG. 4) of the inner cannula cannot rotate over the support ears 204 and 206 when the locking ears are properly engaged with the locking flange 202. For example, in one embodiment the support ears 204 and 206 extend upward from the surface of the locking flange 202 by about 4 mm to about 6 mm (such as about 5 mm) to prevent the engagement mechanism of the inner cannula from rotating over the support ears 204 and 206. Thus, torsional and/or radial movement of the inner cannula connector 310 (FIG. 4) within the outer cannula adapter 200 may be limited or prevented, thereby, preventing loosening and/or breaking of the inner cannula connector 310 (FIG. 4) while it is disposed within the outer cannula adapter 200. Further, such an implementation may prevent the inner cannula connector 310 (FIG. 4) from being bent away from its axial position within the outer cannula by providing additional support where the inner and outer cannulas are engaged.

The snap-flange hood 418 and cannula coupling connector 416 may be attached together by, for example but not limited to, adhesive bonding, ultrasonic bonding, heat staking, solvent bonding; mechanical snaps, threads and pins, etc. Energy directors 420 may be used when the material used for the extended snap-flange hood 418 and coupling flange 416 are ultrasonically welded or heat staked together. The energy directors 420 may be eliminated when the assembly methods used, e.g., solvent bonding, adhesive bonding, or heat staking, spin welding, mechanical snaps or threads, pins, etc., may fuse the snap-flange hood 418 and cannula coupling connector 416 together. Materials that may be used for the cannula coupling connector 416 and snap-flange hood 418 may be, for example but not limited to, polyvinyl chloride (PVC), polycarbonate (such as: Lexan® 104-803), ABS, polystyrene, or other plastic material, metal, carbon fiber, etc.

As described above, when forming the outer cannula coupling connector 416 and the snap flange hood 418 material grade, durometer rating, plasticity, etc., may be chosen for each of the above materials so that the outer cannula coupling connector 416 and the snap flange hood 418 attain the desired mechanical characteristics. Further, the cannula coupling connector 416 and the snap flange hood 418 may be formed using molding techniques, such as techniques suitable for molding solid PVC parts, as discussed above with regard to the generalized discussion of the formation of the outer cannula connector 200.

Figure 4:
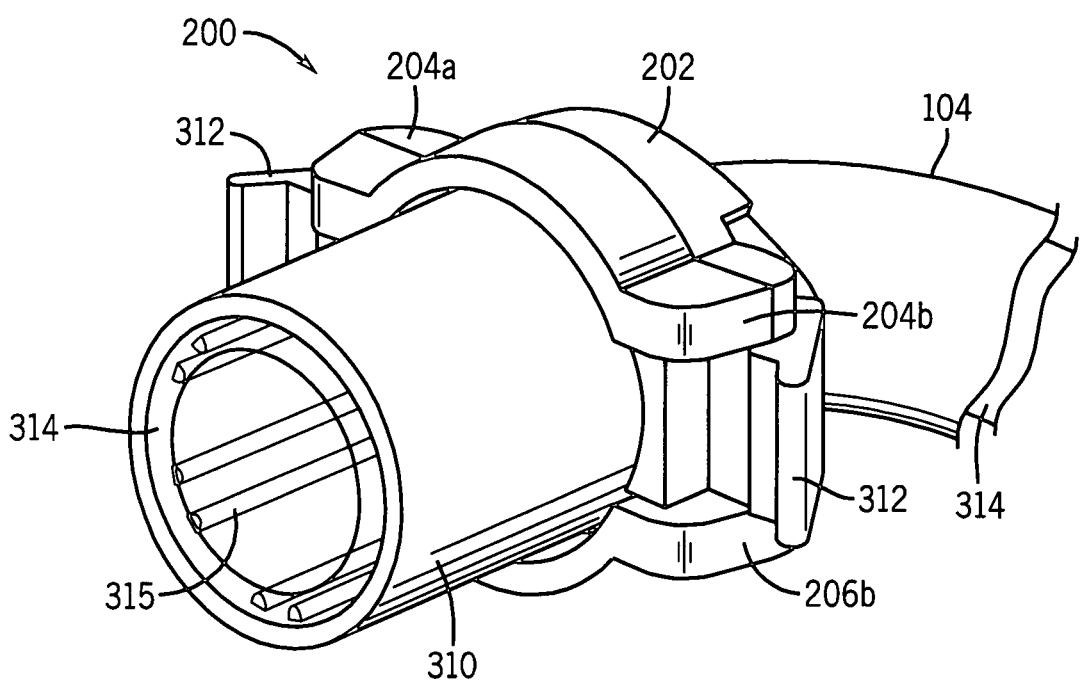
FIG. 4 illustrates a schematic diagram of an inner cannula connector coupled to the outer cannula connector shown in FIG. 2.

Referring to FIG. 4, depicted is a schematic diagram of an inner cannula connector 310 coupled to the outer cannula connector 200 illustrated in FIG. 2. The figure illustrates an inner cannula 314 disposed within an inner cannula connector 310. The inner cannula 314 extends from the opening of the inner cannula connector 310 through the outer cannula locking flange 202 and outer cannula 104 into the patient's trachea (FIG. 1). The inner cannula connector 310 has locking ears 312 that may be adapted to engage the outer cannula locking flange 202. The inner cannula 314 may be inserted into an opening (not shown) in the outer cannula connector 200. Inner cannula connector 310 may be coupled to a proximal end of an inner cannula 314. The inner cannula connector 310 may be adapted for coupling to the ventilator hose 108 (see FIG. 1). For example, ribbed elements 315 may be provided at the interface between the inner cannula connector 310 and the inner cannula 314 that improve the rigidity of the inner cannula connector 310, thereby reducing the risk that the inner cannula connector 310 might distort or buckle when connected to the ventilator hose 108 by a clamp or other biasing mechanism. The inner cannula connector 310 may comprise locking ears 312. A portion of the locking ears 312 and a portion of the inner cannula connector 310 may be placed between the first and second sets of opposing support ears 204 and 206, respectively, and the locking ears 312 may hold, e.g., grasp, clutch, snap, clip, etc., onto the outer cannula locking flange 202. The inner cannula connector 310 may be adapted for coupling to a speaking valve (not shown).

The first and second sets of opposing support ears 204 and 206, respectively, may keep the locking ears 312 substantially aligned therewith, thus preventing rotation of the inner cannula connector 310 within the outer cannula connector 200. The first and second sets of opposing support ears 204 and 206, respectively, may also reduce axial misalignment between the outer cannula connector 200 and the inner cannula connector 310, by preventing substantial torsional radial twisting of the inner cannula connector 310 with respect the outer cannula connector 200. The possibility of locking ears 312 undesirably disengaging, e.g., unlocking, from flange 202 because of rotational and/or radial twisting of the inner cannula connector 310 may be substantially reduced. In the depicted embodiment, prevention of rotation of the locking ears 312 and of the inner cannula connector 310 is accomplished by the presence of support ears 204 and 206 that extend above and outward from the base of the cannula connector 200 and/or the outer locking flange 202. In such an implementation, the locking ears 312 are effectively constrained from rotating when properly engaged with the outer locking flange 202.

The inner cannula connector 310 may be, for example but not limited to, an industry standard inner cannula connector 310 having locking ears 312 that are adapted to lock over, e.g., snap over, the flange 202 (FIG. 2) of a mating outer cannula connector 200. The inner cannula 314 and associated connector 310 may be disposable or reusable. The outer cannula 104 and associated connector 200 may be disposable or reusable.

Like the outer cannula 104 and outer cannula connector 200, the inner cannula connector 310 and inner cannula 314 may be formed from PVC, polycarbonate, ABS, polystyrene, or other plastic materials, metals, carbon fibers, and so forth, having suitable biocompatibility. When forming the inner cannula 314 and/or the inner cannula connector 310, the material grade, durometer rating, plasticity, etc., may be chosen for each of the above materials so that the inner cannula 314 and/or the inner cannula connector 310 has the desired mechanical characteristics, such as rigidity, flexibility, and so forth.

The inner cannula 314 may be formed using injection molding techniques or other conventional molding techniques used to shape and form the desired material, such as PVC, or by the application of heat and tension to conventional tubing, such as PVC tubing, to stretch and shape an existing piece of tubing. For example, a tube of material (such as PVC in one example) in a moldable state (such as in a molten state) may be inserted into a mold having a specified shape, i.e., length, curvature, tube circumference and so forth, corresponding to the inner cannula 314. While in the mold, air may be injected at pressure into the molten tube, forcing the tube into conformity with the mold such that, upon setting and removal from the mold, an inner cannula 314 having the desired characteristics is formed. Alternatively, a length of PVC tubing shorter than the ultimate length of the inner cannula 314 may be heated to a tractable or otherwise deformable state while tension is applied to the PVC tube, thereby allowing the tube to be stretched and shaped to form the inner cannula 314.

The inner cannula connector 310 is formed from PVC having a higher durometer than the corresponding inner cannula 314, i.e., the inner cannula connector 310 is harder than the inner cannula 314. In one such implementation, the inner cannula connector 310 is formed, for example, by molding techniques, such as conventional molding techniques used to shape and form solid PVC parts. For example, a quantity of material (such as PVC in one example) in a moldable state (such as in a molten state) may be injected into a mold having a specified shape, i.e., dimensions, shape, curvature and so forth, corresponding to the inner cannula connector 310. Upon setting and removal from the mold, an inner cannula connector 310 having the desired characteristics is formed.

In combining the inner cannula 314 and the inner cannula connector 310 to form a single structure, the inner cannula 314 may be press fitted with the inner cannula connector 310 such that the top portion of the inner cannula 314 is securely attached to the inner cannula connector 310. In one embodiment, such press fitting may be achieved by bringing the inner cannula 314 to its softening temperature and pulling the softened inner cannula 314 through the inner cannula connector 310 such that, upon cooling, the inner cannula 314 and inner cannula connector 310 are securely attached. For example, if PVC is used to from the inner cannula, the softening temperature of the PVC may depend on the grade, plasticity etc., of the PVC. Typical softening temperatures for a PVC inner cannula 314 may vary, depending on the plasticity of the PVC used in forming the inner cannula 314. Such a softening temperature may be attainable during forming or not long after the inner cannula connector is molded or otherwise formed. For example, the inner cannula 314 may be formed at high temperature such that the material forming the inner cannula 314 is molten or softened. Before the inner cannula 314 is fully cooled after forming, such as while still at a softened temperature, the inner cannula may be pulled through the inner cannula connector 310 and pressed to the inner cannula connector 310 to form the secure attachment between the inner cannula 314 and the inner cannula connector 310. In such an embodiment, the inner cannula 314 is press-fitted through the inner cannula connector 310 such that a terminal portion of the inner cannula 314 is threaded through the opening of the inner cannula connector 310. Once set, the inner cannula 314 and the inner cannula connector 310 are securely bonded so as to effectively form a single structure.

In an exemplary embodiment, the outer cannula 104, the snap flange hood, the inner cannula 314 and the inner cannula connector 310 may be formed according to certain specifications which may include certain materials having specific parameters (such as durometer ratings, specific gravity, etc.), molding processes and so forth. For example, in an exemplary embodiment, the above mentioned tracheotomy tube components may be made using the following materials and aforementioned parameters, summarized in Table 1:

TABLE 1

| | Material Used | Hardness (durometer rating) | Specific Gravity | Molding Process |
|---|---|---|---|---|
| Outer Cannula (104) | PVC | 60 ± 2 Per ASTM D2240 | 1.42 ± .01 | Injection Molding |
| Inner Cannula (314) | PVC | 87 ± 2 Per ASTM D2240 | 1.26 ± 0.1 | Injection Over-Molding |
| Inner Cannula Connector (310) | Polypropilene (PP) REXENE ® 13R9A Clear Resin | 90 Per ASTM D785 | 0.902 ± 0.1 Per ASTM D792 | Injection Molding |
| Snap Flange Hood (418) | Polycorbonate Comp-Wht (Lexan ® 104-803) | 70 ± 2 Per ASTM D785 | 1.2 ± 0.1 Per ASTM D792 | Injection Molding |
| Neck Flange (106) | PVC | 60 ± 2 | 1.42 ± 0.1 | Injection Molding |

An exemplary method of forming the inner cannula 314 and the inner cannula connector 310 may include, forming the inner cannula connector 310 through injection molding, whereby molten polypropylene is injected into a mold conforming to the shape of the inner cannula connector 310. Thereafter, the molded inner cannula connector 310 may be set to cool down to a suitable temperature so that it can be placed and/or incorporated within a mold used for over molding the inner cannula 314. The mold used for overmolding the inner cannula 314 is shaped to correspond to the desired shape of inner cannula 314 and may include an interior spacer that corresponds to the passage through the inner cannula 314 when formed. Thereafter, injection molding may be performed, whereby PVC is injected throughout the mold of the inner cannula 314 for forming the inner cannula 314. In addition, by incorporating the newly formed inner cannula connector 310 with the mold of the inner cannula 314, the PVC forming the inner cannula 314 may adhere to the polypropylene forming inner cannula 310, such that those two components form a single structure.

As will be appreciated by those skilled in the art, the inner cannula connector 310 may be overmolded using an injection molding machine. Such an injection molding machine may be configured with certain parameter settings, such as molding temperature, molding pressure and so forth, to provide the above mentioned molded structures having the desired shape and material characteristics. Those skilled in the art will appreciate, for example, that during overmolding of the PVC inner cannula, the injection nozzle and barrel of the injection molding machine may be maintained at temperatures ranging between 325-350 degrees Fahrenheit. In addition, nozzle pressure used for pressing the PVC molding material, in this example, as it exits the injection molding machine may be set between 300-600 pounds per square inch (psi), with pressure limits set between 1300-1700 psi. Further, in forming a polypropylene inner cannula connector, the nozzle and barrel temperatures of the injection molding machine may be maintained between 570-590 degrees Fahrenheit, while injection boost pressure may be set between 1508-2000 psi and holding pressure may be set to approximately 1400 psi.

Similarly, a PVC outer cannula may be formed using an injection molding machine in which the barrel and nozzle are maintained at temperatures ranging between 320-340 Fahrenheit. Injection boost pressure used for molding such a PVC outer cannula may range between 1300-2000 psi, while holding pressure may be set to approximately 860 psi. Further, in forming a neck flange, barrel and nozzle temperature may be set to approximately 350 Fahrenheit, while injection hold pressure may be set to 1500 psi.

It should be born in mind that the aforementioned molding materials and parameters of the components of the tracheotomy tube, such as those listed in table 1 above, are exemplary and may be subject to change in accordance with design and/or manufacturing modifications, constraints and/or varying operational requirements.

Figure 5:
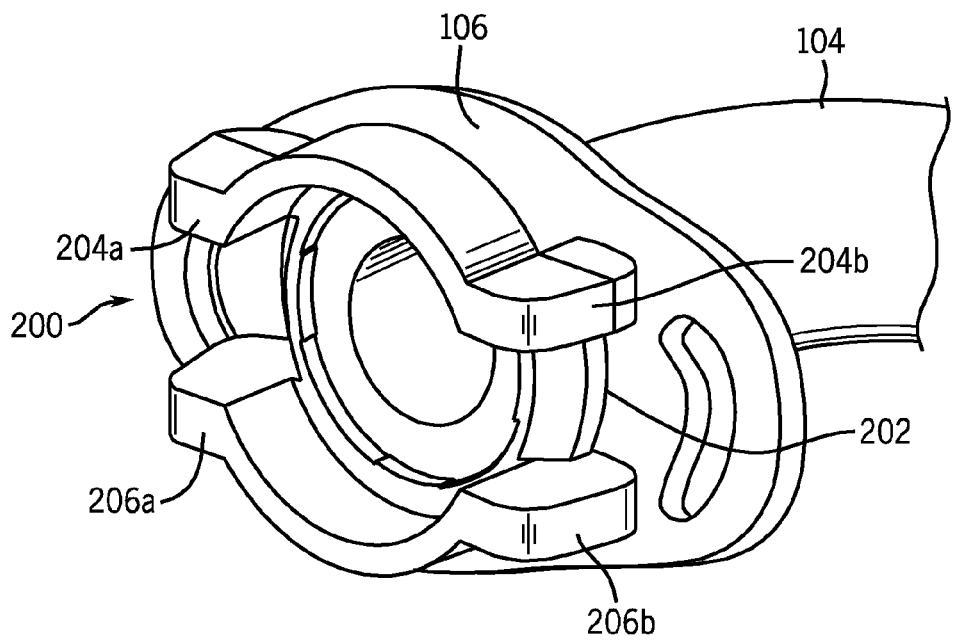
FIG. 5 illustrates a schematic diagram of an outer cannula connector without an inner cannula inserted, in accordance with an embodiment of the present technique.

Referring to FIG. 5, depicted is a schematic diagram of an outer cannula connector without an inner cannula inserted. The neck flange 106 may be positioned in, e.g., snapped onto, the outer cannula connector 200. As described above and as depicted in FIG. 5, the support ears 204 and 206 extend above and outward from the locking flange 202 such that, when the complementary engagement structures of the inner cannula are properly engaged with the outer cannula connector 200, the engagement structures of the inner cannula are prevented from rotating or twisting relative to the outer cannula 104.

Materials that may be used for the neck flange 106 may be, for example but not limited to, polyvinyl chloride (PVC), polycarbonate, ABS, polystyrene, or other plastic material, metal, carbon fiber, etc. that have suitable biocompatibility. When forming the neck flange 106, material grade, durometer rating, plasticity, etc., may be chosen for each of the above materials so that the outer neck flange 106 attains desired mechanical characteristics. Further, the neck flange 106 may be formed using suitable molding techniques for the material employed, such as suitable molding techniques for forming a solid PVC part, as discussed above.

Figure 6:
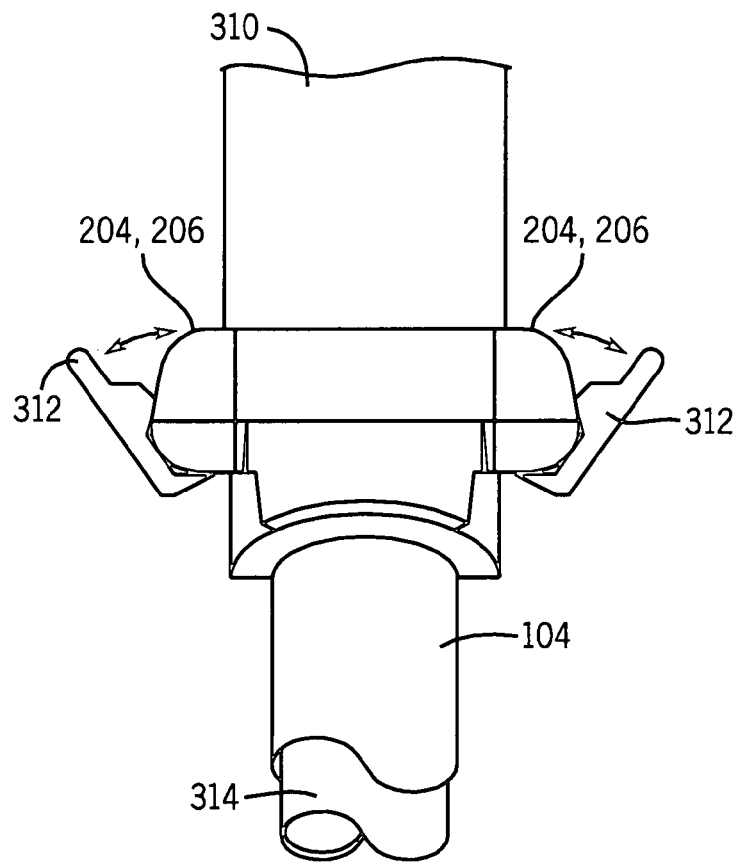
FIG. 6 illustrates a schematic diagram of an inner cannula connector having locking ears supported by opposing sets of support ears of the outer cannula connector, according to a specific example embodiment of the present disclosure.

Referring to FIG. 6, depicted is a schematic diagram of an inner cannula connector having locking ears supported by opposing sets of support ears of the outer cannula connector, according to a specific example embodiment of the present disclosure. In this specific example embodiment, the inner cannula locking ears 312 fasten or connect with, e.g., snap, over flanges 202 (see FIGS. 2 and 4) that are between the first and second sets of support ears 204 and 206, respectively. Placing the locking ears 312 of the inner cannula connector 310 between the first and second sets of opposing support ears 204 and 206, respectively, substantially prevents the locking ears 312 from undesirably disengaging, e.g., unlocking, from the flanges 202, for example, because of twisting and/or radial torque on the inner cannula connector 310. That is, the height of the supporting ears 204 and 206 above the base of the outer cannula adapter, their radial extension beyond the locking flange 202, and providing spacing between the support ears 204 and 206 that corresponds to the width of the locking ears 312 secures the locking ears 312 in place, preventing the displacement of the inner cannula 310.

Figure 7:
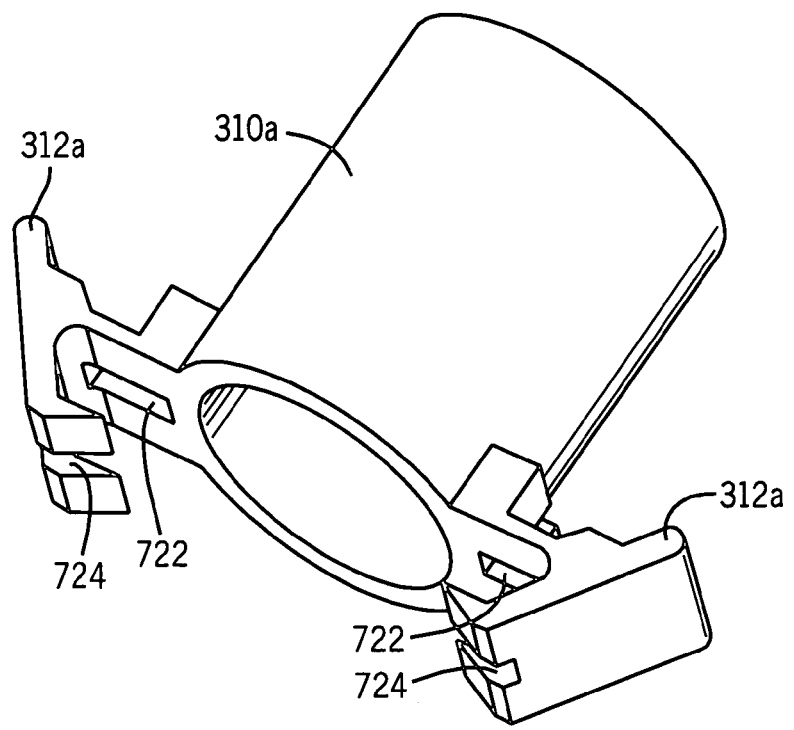
FIG. 7 illustrates a schematic diagram of an inner cannula connector having locking ears with slots adapted for receiving opposing support ears of an outer cannula connector, according to another specific example embodiment of the present disclosure.
Figure 8:
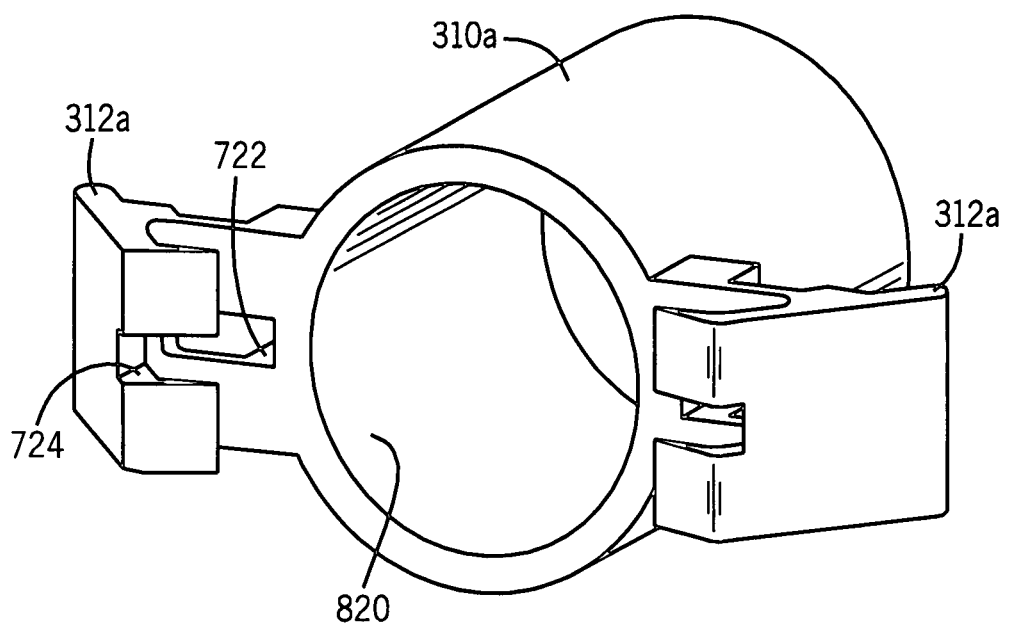
FIG. 8 illustrates a schematic diagram of the inner cannula connector shown in FIG. 6.
Figure 9:
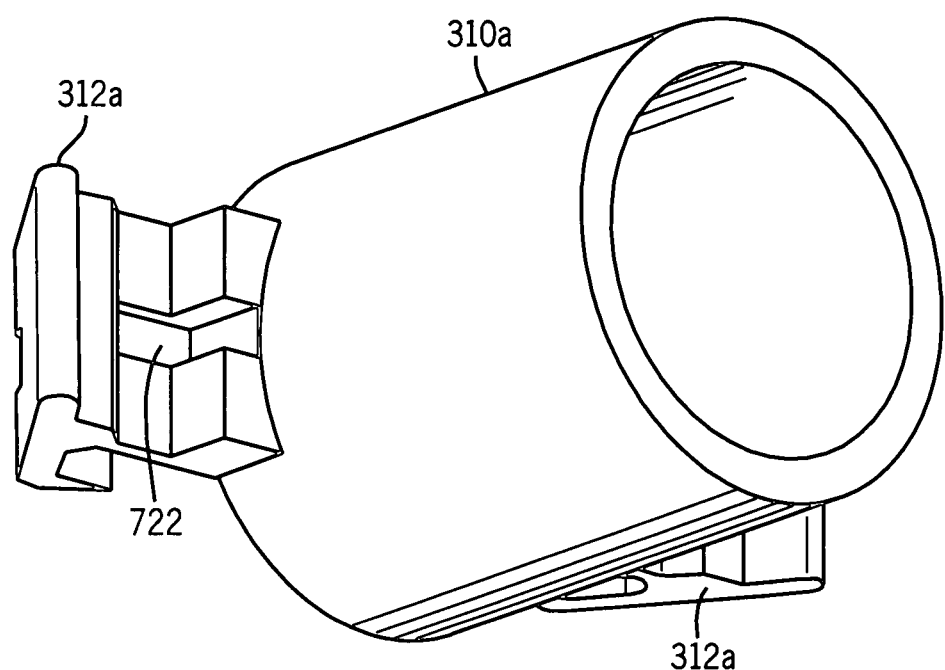
FIG. 9 illustrates a schematic diagram of an opposite view of the inner cannula connector shown in FIG. 6.

Referring now to FIGS. 7-9, depicted are schematic diagrams of an inner cannula connector having locking ears with slots adapted for receiving opposing support ears of an outer cannula connector, according to another specific example embodiment of the present disclosure. An inner cannula connector 310a has locking ears 312a that may be adapted to engage an outer cannula locking flange (e.g., locking flange 202 or locking flange 1012 shown in FIGS. 10-14). The inner cannula connector 310a is attached to a proximal end of an inner cannula and the inner cannula may be inserted into an outer cannula connector (e.g., connector 200 or connector 1000 of FIG. 10). The inner cannula connector 310a may be adapted for coupling to the ventilator hose 108 (see FIG. 1). The locking ears 312a may hold, e.g., grasp, clutch, snap, clip, etc., onto the outer cannula locking flange 202 or locking flange 1012. When placed onto the outer cannula locking flange 202, a portion of the locking ears 312a and a portion of the inner cannula connector 310a may be placed between the first and second sets of opposing support ears 204 and 206, respectively. When placed onto the outer cannula locking flange 1012 shown in FIGS. 10-14, slots 722 and 724 may receive opposing support ears 1014 as shown in FIGS. 10-14. Thus, the inner cannula connector 310a may be used with either the outer cannula connector 200 described hereinabove, or an outer cannula connector 1000 described hereinafter.

Figure 10:
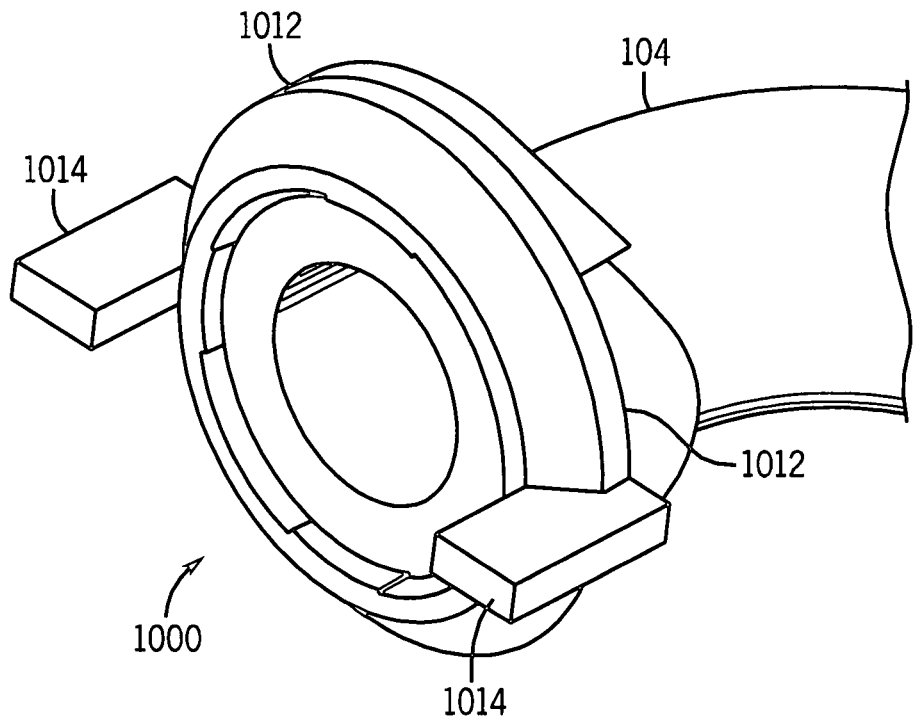
FIG. 10 illustrates a schematic diagram of an outer cannula connector comprising a locking flange having opposing support ears, according to the another specific example embodiment of the present disclosure.
Figure 11:
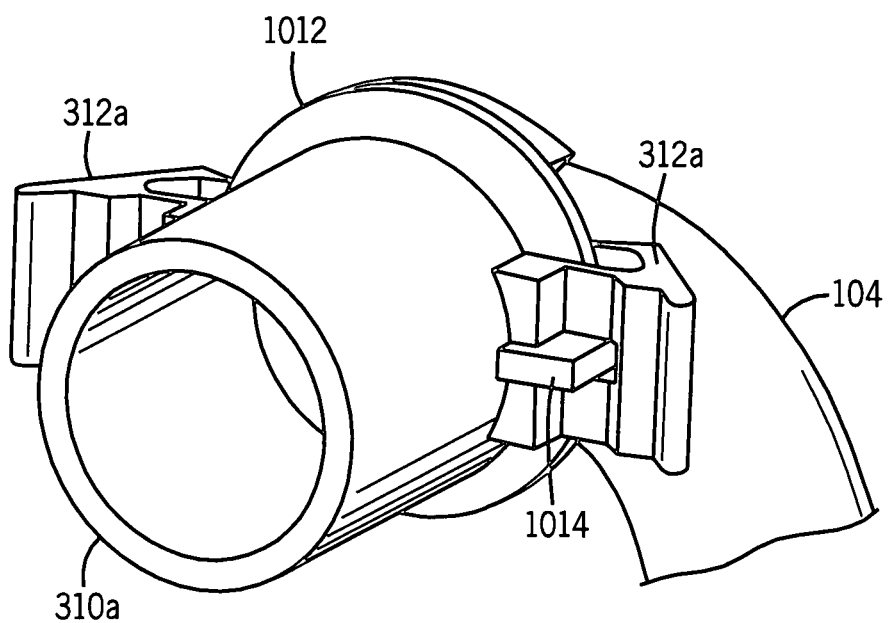
FIG. 11 illustrates a schematic diagram of the outer cannula connector shown in FIG. 10 and inner cannula connector shown in FIGS. 7-9 coupled together.

Referring now to FIG. 10, depicted is schematic diagram of an outer cannula connector comprising a locking flange having opposing support ears, according to another specific example embodiment of the present disclosure. An outer cannula connector, generally represented by the numeral 1000, comprises an outer cannula locking flange 1012 and opposing support ears 1014, e.g., tabs, prongs, pins, etc. The outer cannula connector 1014 may be coupled to a proximal end of the outer cannula 104.

Referring now to FIGS. 11-14, depicted are schematic diagrams at various views of the outer cannula connector shown in FIG. 10 and inner cannula connector shown in FIGS. 7-9 coupled together. The opposing support ears 1014 may slidingly engage into the slots 722 and 724 (FIGS. 7-9) in the locking ears 312a of the inner cannula connector 310a. The opposing support ears 1014 may substantially prevent the locking ears 312a from twisting off of the locking flange 1012 due to, for example, twisting and/or radial torque on the inner cannula connector 310a.

Figure 12:
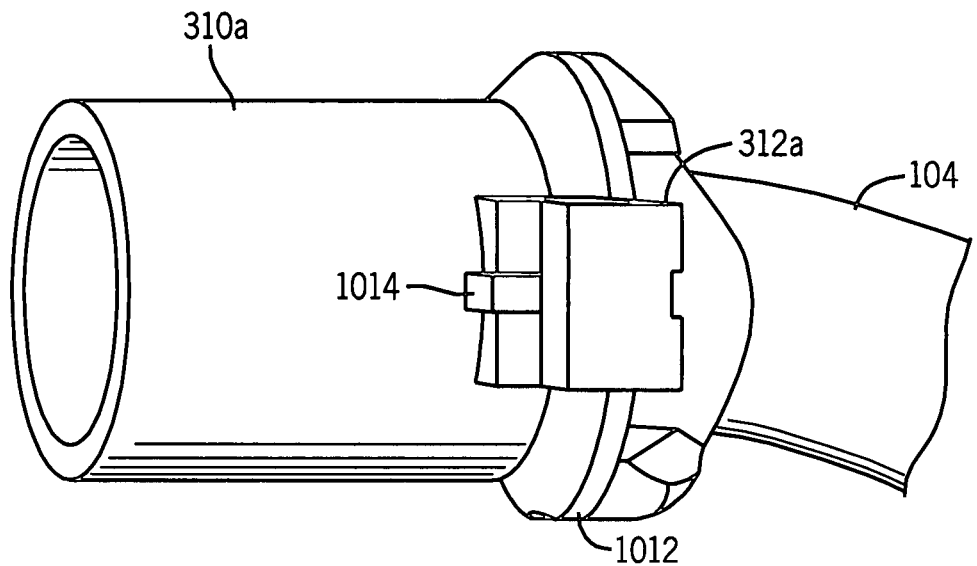
FIG. 12 illustrates a schematic side view diagram of the outer and inner cannula connectors shown in FIG. 10.
Figure 13:
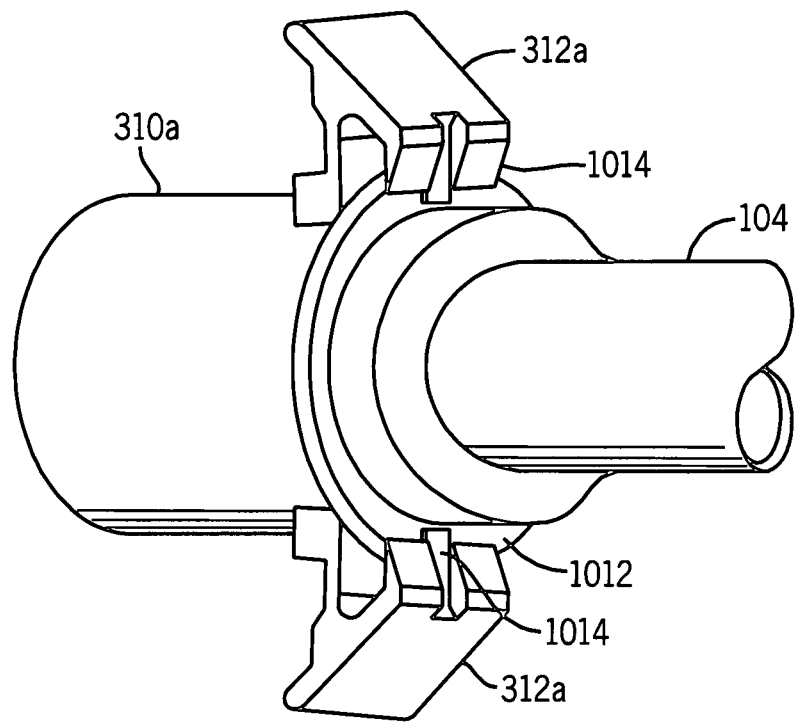
FIG. 13 illustrates another schematic diagram side view of the outer and inner cannula connectors shown in FIG. 10.
Figure 14:
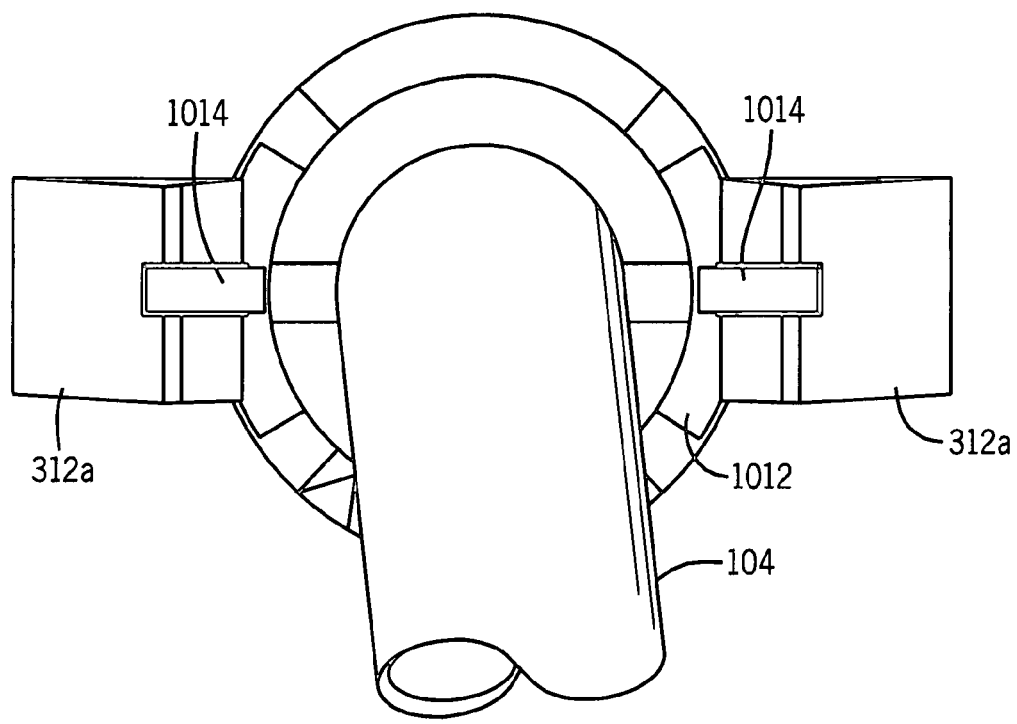
FIG. 14 illustrates a schematic diagram back view of the outer cannula connector shown in FIG. 10 with the inner cannula locking ears engaging the locking flange of the outer cannula connector.

FIG. 12 illustrates a schematic side view diagram of the outer and inner cannula connectors shown in FIG. 10. FIG. 13 illustrates another schematic diagram side view of the outer and inner cannula connectors shown in FIG. 10. FIG. 14 illustrates a schematic diagram back view of the outer cannula connector shown in FIG. 10 with the inner cannula locking ears engaging the locking flange of the outer cannula connector.

Specific example embodiments, according to this disclosure may restrict axial rotation of the inner cannula from a centered position for example, but not limited to, at a minimum of about +/−0.5 degrees, as much as +/−2 degrees, and possibly as much as +/−10 degrees rotation. Specific example embodiments, according to this disclosure may restrict longitudinal movement for example, but not limited to, at a minimum of about +/−0.005 inches (+/− about 0.127 mm), as much as +/−0.010 inches (+/− about 0.254 mm), and possibly as much as +/−0.10 inches (+/− about 2.54 mm) without substantial disengagement.

In the illustrated embodiments, axial rotations of the inner cannula connector with respect to the outer may be restricted such that substantially no rotation, i.e., zero degrees of rotations, is permitted between the inner cannula connector 310 and the outer cannula connector 200 when those structures are securely engaged. Similarly, in certain embodiments, substantially no longitudinal movement is permitted between the inner cannula connector 310 and the outer cannula connector 200 when those structures are securely engaged.

Figure 15:
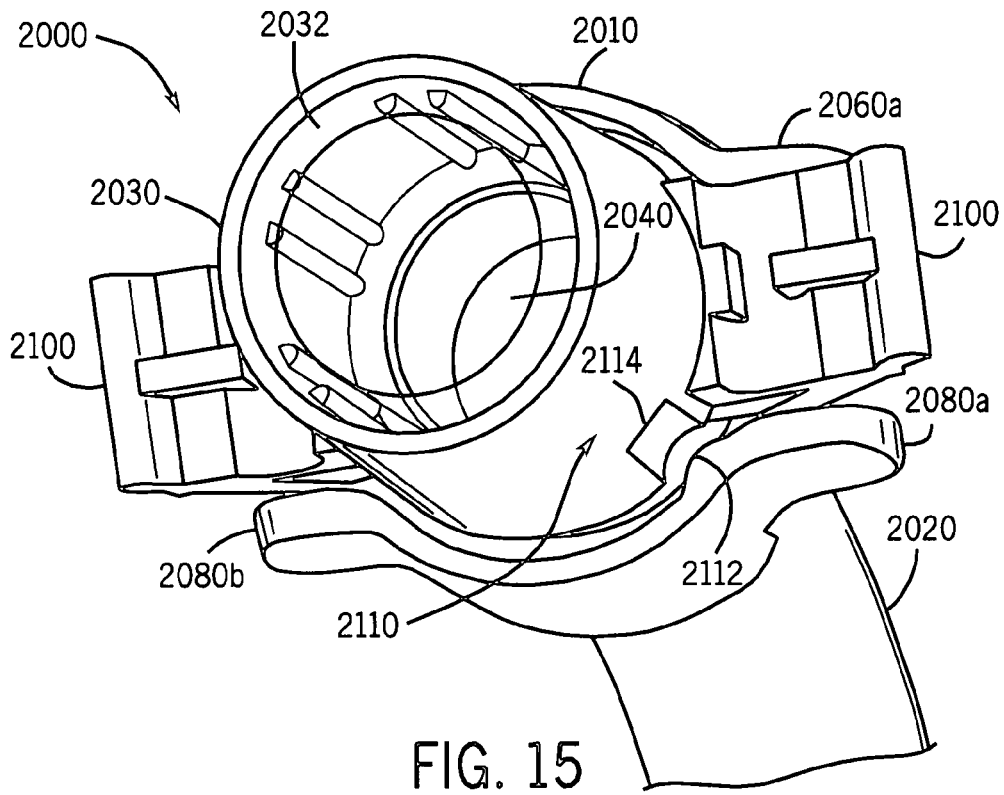
FIG. 15 illustrates a schematic diagram of an inner cannula connector coupled to an outer cannula connector having a matching keying feature, in accordance with an embodiment of the present technique.

In an additional embodiment of the present technique, the inner and outer cannulas are provided with a keying feature corresponding to the respective sizes of the inner and outer cannulas. For example, FIG. 15 illustrates an inner cannula connector coupled to an outer cannula connector having a matching keying feature, in accordance with an embodiment of the present technique. Accordingly, FIG. 15 depicts an outer cannula connector 2000 including an outer cannula engagement structure 2010, an outer cannula 2020 and an inner cannula connector 2030. The inner cannula connector 2030 is coupled to an inner cannula 2032 (shown as transparent) inserted within the outer cannula 2020. The inner cannula connector 2030 has an opening 2040 through which air can flow through the combination of the inner and outer cannulas and into a patient's trachea. In the illustrated embodiment, the inner cannula 2032 may be formed of plastic materials, i.e., PVC of a certain grade, rendering it relatively more transparent/clear with respect to the outer cannula 2020 or the inner cannula connector 2030.

Further, the outer cannula engagement structure 2010 includes two pairs of support ears 2060a, 2060b and 2080a, 2080b, as previously described. Similar to the embodiment shown in FIG. 4, the support ears 2060a, 2060b, 2080a and 2080b extend above and radially outward from the base of the outer cannula engagement structure 2010, forming two diametrically opposed restraining structures adapted to prevent rotation of locking ears 2100 of the inner cannula connector 2030, as further discussed below. The supporting ears 2060a, 2060b and/or 2080a, 2080b form continuous structures that partially encompass the circumference of the outer cannula connector 2000. The outer edges of the support ears 2060a, 2060b and/or 2080a, 2080b extend radially beyond the outer cannula connector 2000.

As described above, the inner cannula connector 2030 may include locking ears 2100. A portion of the locking ears 2100 and a portion of the inner cannula connector 2030 may be placed between the first and second sets of opposing support ears 2060 and 2080, respectively, and the locking ears 2100 may hold, e.g., grasp, clutch, snap, clip, etc., onto an outer cannula locking flange, as described above.

The two opposing support ear structures 2060 and 2080, respectively, are securely disposed about each of the locking ears 2100, such that the locking ears fit securely within the retaining structures formed by the support ears 2060 and 2080. In this manner, the locking ears 2100 remain substantially aligned with the outer cannula connector 2000 and with the pair of supporting ears 2060 and 2080, thus, preventing rotation, jerking or swivel of the inner cannula connector 2030 within the outer cannula connector 2000. Further, the pair of opposing support ears 2060 and 2080, respectively, may also reduce axial misalignments between the outer cannula flange 2010 and the inner cannula connector 2030. This may prevent substantial torsional twisting of the inner cannula connector 2030 with respect to the outer cannula connector 2000. As a result, the possibility of locking ears 2100 undesirably disengaging, e.g., unlocking, from the outer cannula engagement structure 2010 because of rotational and/or radial twisting of the inner cannula connector 2030 may be substantially reduced.

In the illustrated embodiment, the outer cannula connector 2000 further includes a keying feature 2110 which, in one embodiment, is formed of a protrusion 2112 and a corresponding or complementary recess 2114. In one implementation, the protrusion 2112 is disposed on the outer cannula engagement structure 2010. The protrusion 2112 may be formed of a post, pin, rib, bump or ridge of material such that it may fit securely within the complementary recess 2114. Accordingly, the recess 2114 is disposed on the inner cannula connector 2030. The recess 2114 may be adapted to receive and/or mate with any of the above mentioned types of protrusion 2112, so as to lock the inner cannula connector 2030 with the outer cannula engagement structure 2010. In so doing, the outer cannula connector 2000 will allow an appropriately keyed inner cannula connector 2030 to be inserted into the outer cannula engagement structure 2010.

Such a keying feature 2110 may be desirable when the inner and outer cannula connectors are so keyed that only appropriately sized inner cannulas may be inserted into an outer cannula. In other words, each size of outer cannula connector 2000 and the corresponding inner cannula connector 2030 are keyed in a complementary manner such that other sizes of inner cannula connector 2030 cannot be inserted into and engaged with the outer cannula connector 2000. For example, the present technique may prevent the insertion of a #4 sized inner cannula into a #8 sized outer cannula and so forth.

As will be appreciated, the complementary nature of the keying features 2110 (in the depicted example, protrusion 2112 and recess 2114) of the outer cannula connector 2000 and the inner cannula connector 2030 may be based upon different physical or positional characteristics. For example, in some embodiments, the complementarity of the keying features 2110 may be based upon the size and/or shape of the respective keying features 2110. For example, different polygonal, oval, and/or round protrusions 2112 and complementary recesses 2114 and/or different sizes of protrusions 2112 and complementary recesses 2114 may be provided to prevent mismatches between inner and outer cannula connectors 2030 and 2000. In addition, different angular or radial placement of the keying features 2110 may be employed to prevent such mismatches. For example, the keying feature 2110 may be "clocked" at varying degrees of rotation around the outer cannula connector 2000, as further discussed below with respect to FIG. 17. In one such implementation, the keying features 2110 for different sizes of inner and outer cannula connectors 2000 and 2030 may be positioned at different radial positions about the outer cannula engagement structure 2010 and the inner cannula connector 2030 to provide unique complementary configurations for each acceptable combination of outer and inner cannula connectors 2000 and 2030.

In addition, keying features 2110, such as those mentioned above with respect to the outer cannula connector, may include identifying features thereby distinguishing inner cannulas and/or outer cannulas of different sizes. For example, such identifying features may enable identifying a #4, #6, #8 size, etc., inner cannulas based on the location, size and/or shape of the keying feature on the inner cannula connector 2030. This may enable a healthcare provider to expediently identify proper size inner cannulas, as well as prevent inadvertent insertions of an inner cannula having a too-small diameter into an outer cannula connector.

Figure 16:
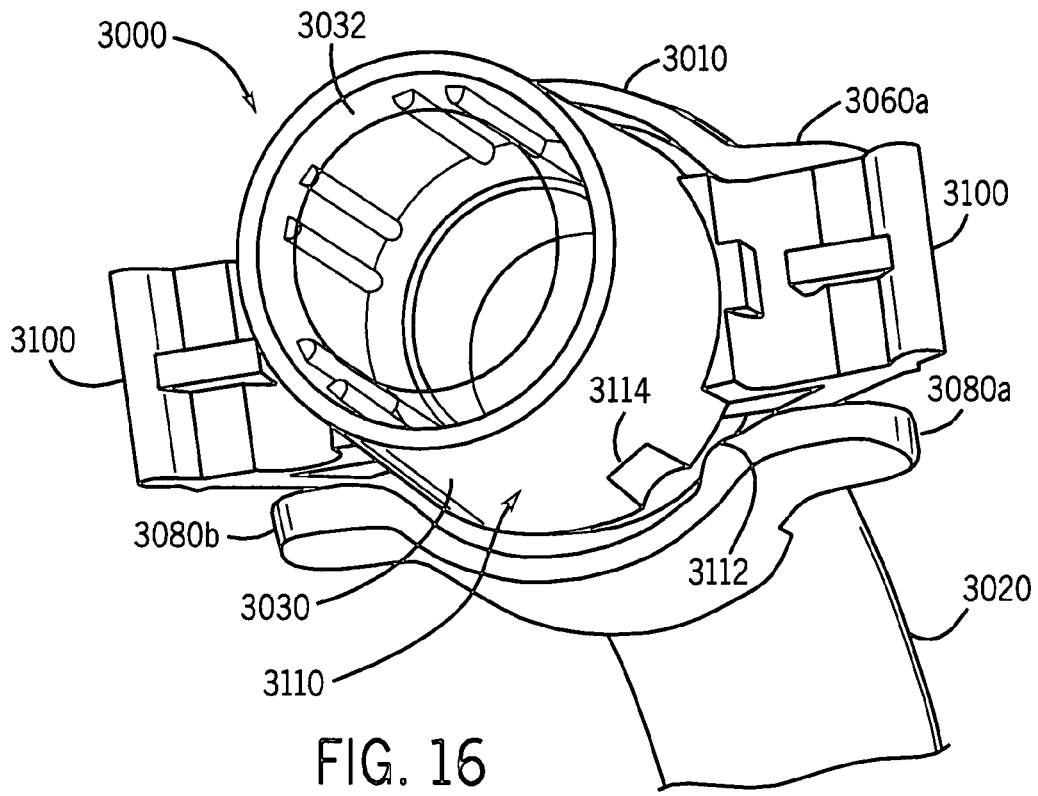
FIG. 16 illustrates an inner cannula connectors coupled to outer cannula connectors having a mismatched keying feature, in accordance with an embodiment of the present technique.

With the foregoing discussion in mind, FIG. 16 illustrates an inner cannula connector which is improperly inserted into an outer cannula connector having a mismatched keying feature 3110. In this example, an outer cannula connector 3000 is depicted having an outer cannula engagement structure 3010, an outer cannula 3020, an inner cannula connector 3030 and an inner cannula 3032 disposed within the inner cannula connector 3030. The illustrated embodiment further includes a mismatched keying feature 3110 in which a protrusion 3112 on the outer cannula connector 2000 does not complement or otherwise correspond with a recess 3114 on the inner cannula connector 2030.

In particular, in the depicted implementation, FIG. 16 illustrates an inner cannula connector 2030 that is inserted into an outer cannula connector 3000 of the wrong size, i.e., the respective inner and outer cannulas are different sizes. In such an implementation, the mismatched keying features 3110 prevent full insertion of inner cannula in the outer cannula and, therefore, the inner cannula connector 3030 cannot be secured to the outer cannula connector 3000. For example, in the depicted embodiment, a protrusion 3112 on the outer cannula connector 2000 is radially displaced from a recess 3114 on the inner cannula connector 2030. As a result, the protrusion 3112 and the recess 3114 of the mismatched keying feature 3110 are not complementary and the inner cannula connector 3030 cannot be inserted into the outer cannula connector 3000. In particular, the structural mismatch between the protrusion 3112 and the recess 3114 and the orientation of the inner cannula connector 3030 imposed by the alignment of the locking ears 3100 and the support ears 3060 and 3080 prevent full insertion of the inner cannula connector 3030 into the outer cannula connector 3000. In such an implementation, the inability of a technician to fully insert the inner cannula connector 3030 into the outer cannula connector informs the technician of the size mismatch, thereby prompting the clinician to select an appropriately sized inner cannula.

Figure 17:
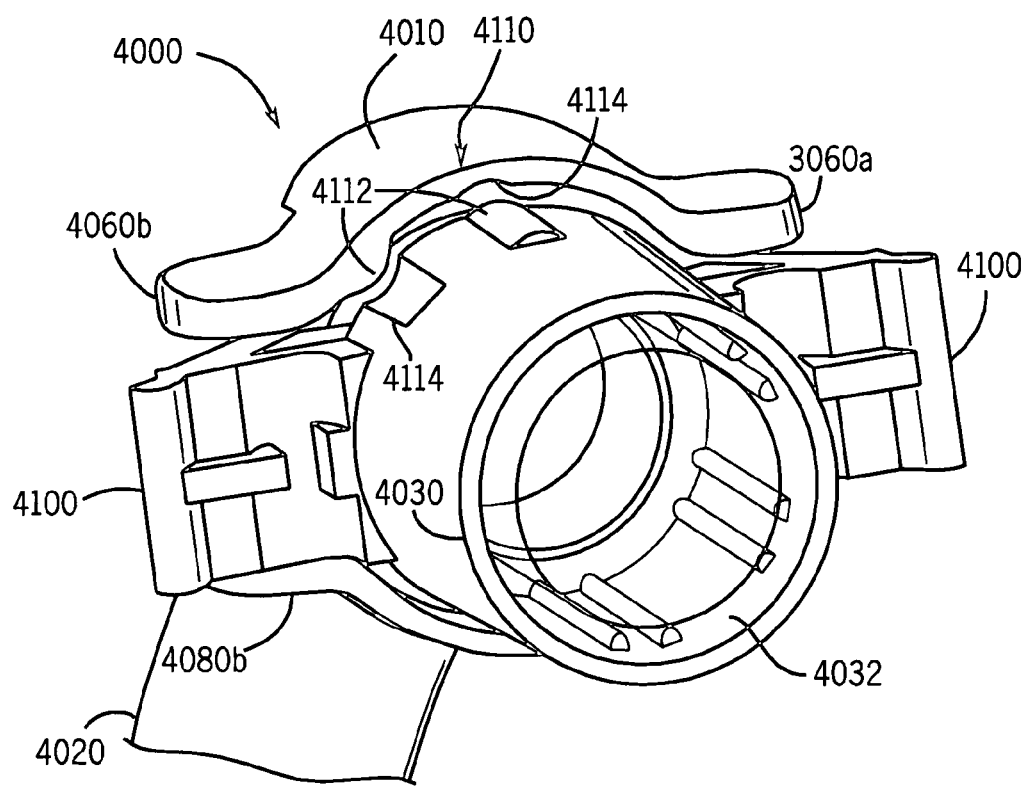
FIG. 17 illustrates another inner cannula connector coupled to an outer cannula connector having a plurality of keying features in accordance with an embodiment of the present technique.

FIG. 17 illustrates an inner cannula connector coupled to an outer cannula connector having a plurality of keying feature, in accordance with an exemplary embodiment of the present technique. The figure depicts an outer cannula connector 4000 having an outer cannula engagement structure 4010, an outer cannula 4020, an inner cannula connector 4030 and an inner cannula 4032 disposed within the outer cannula 4020. Similar to the embodiment depicted in FIG. 16, the illustrated embodiment includes inner cannula airway opening 4040, a pair of support ears 4060a/b, 4080a/b and locking ears 4100. The illustrated embodiment further includes a plurality keying features 4110 and 4111 disposed the outer cannula connector 4000. While illustrated in the FIG. 17 are the two keying features 4110 and 4111, additional keying features such as the latter may be disposed at other locations about the outer cannula connector 4000. For example, multiple keying features, such as 4110 and 4111, may be evenly (clocked) or unevenly spaced from each other about the outer cannula connector 4000. Such configurations may enhance the secure fitting of the inner cannula connector 4030 to the outer cannula engagement structure 4010.

As further illustrated, keying feature 4110 includes protrusion 4112 disposed on the outer cannula engagement structure matched with recess 4114 disposed on the inner cannula connector 4030. Keying feature 4111 includes matching protrusion 4112 and recess portion 4114 similar to those forming keying feature 4110. However, unlike keying feature the 4110 the keying feature 4111 is formed such that the recess 4114 is disposed on the outer engagement structure 4010 and the protrusion 4112 is disposed on the inner cannula connector 4030. Accordingly, some embodiments may include disposing keying features 4110 and 4111 in an alternating pattern about the outer cannula connector 4000. Such features may further promote the secure fastening of inner to outer cannulas.

While embodiments of this disclosure have been depicted, described, and are defined by reference to example embodiments of the disclosure, such references do not imply a limitation on the disclosure, and no such limitation is to be inferred. The subject matter disclosed is capable of considerable modification, alteration, and equivalents in form and function, as will occur to those ordinarily skilled in the pertinent art and having the benefit of this disclosure. The depicted and described embodiments of this disclosure are examples only, and are not exhaustive of the scope of the disclosure.

What is claimed is:

1. A cannula assembly kit, comprising:
   a first inner cannula; and
   a first inner cannula connector associated with the first inner cannula comprising a first keying feature and a second keying feature radially distributed about the first inner cannula connector with a first clocking pattern
   an outer cannula coupled to an outer cannula connector comprising a locking flange forming a complete annulus and comprising complementary features configured to engage the first keying feature and the second keying feature, wherein a clocking pattern of the complementary features allows mating of the first inner cannula connector and the outer cannula connector; and
   a second inner cannula connector associated with a second inner cannula comprising a plurality of keying features radially distributed about the second inner cannula connector with a second clocking pattern configured to prevent mating of the second inner cannula connector with the outer cannula connector such that the plurality of keying features is not compatible with the complementary features of the outer cannula connector.

2. The cannula assembly kit according to claim 1, wherein the first clocking pattern corresponds to the first inner cannula of a certain size.

3. The cannula assembly kit according to claim 1, wherein at least one of the complementary features is positioned at a location on the outer cannula connector that corresponds with a size of the outer cannula.

4. The cannula assembly kit according to claim 1, wherein at least one of the complementary features comprises a shape that corresponds with a size of the outer cannula.

5. The cannula assembly kit according to claim 1, wherein the complementary features extend radially outward from the locking flange.

6. The cannula assembly kit according to claim 1, wherein at least a portion of the locking flange is between the first keying feature and the second keying feature when the outer cannula connector is engaged with the first inner cannula connector.

7. The cannula assembly kit according to claim 1, wherein the complementary features prevent rotation of the first inner cannula connector when the first inner cannula connector is engaged with the outer cannula connector.

8. The cannula assembly kit according to claim 1, wherein the first keying feature comprises a first passageway and the second keying feature comprises a second passageway, each configured to receive at least one of the complementary features.

9. The cannula assembly kit according to claim 8, wherein the first passageway and the second passageway extend from an interior surface of each respective body corresponding to the first keying feature and the second keying feature completely through to an exterior surface of the respective body.

10. The cannula assembly kit according to claim 8, wherein the complementary features are configured to extend through the respective first and second passageways such that the first keying feature and the second keying feature abut the locking flange when engaged with the complementary features.

11. The cannula assembly kit according to claim 8, wherein a size of the first passageway and the second passageway corresponds to a size of the first inner cannula.

12. The cannula assembly kit according to claim 1, wherein the first keying feature and the second keying feature extend from opposing sides of the inner cannula connector.

13. The cannula assembly kit according to claim 1, wherein the second clocking pattern corresponds to the second cannula of a certain size.

14. The cannula assembly kit according to claim 1, wherein the plurality of keying features each comprises a passageway corresponding to a size of the second inner cannula.

* * * * *